(12) United States Patent
Heruth et al.

(10) Patent No.: US 7,330,760 B2
(45) Date of Patent: *Feb. 12, 2008

(54) COLLECTING POSTURE INFORMATION TO EVALUATE THERAPY

(75) Inventors: Kenneth T. Heruth, Edina, MN (US); Keith A. Miesel, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 472 days.

This patent is subject to a terminal disclaimer.

(21) Appl. No.: 10/826,926

(22) Filed: Apr. 15, 2004

(65) Prior Publication Data

US 2005/0209645 A1      Sep. 22, 2005

Related U.S. Application Data

(60) Provisional application No. 60/553,784, filed on Mar. 16, 2004.

(51) Int. Cl.
*A61N 1/00* (2006.01)

(52) U.S. Cl. .............................. 607/17; 607/18; 607/19

(58) Field of Classification Search ............. 607/17–19
See application file for complete search history.

(56) References Cited

U.S. PATENT DOCUMENTS

| | | | |
|---|---|---|---|
| 4,297,685 A | 10/1981 | Brainard, II | |
| 4,550,736 A | 11/1985 | Broughton et al. | |
| 4,771,780 A | 9/1988 | Sholder | |
| 4,776,345 A | 10/1988 | Cohen et al. | |
| 4,846,195 A | 7/1989 | Alt | |
| 5,040,536 A | 8/1991 | Riff | |
| 5,058,584 A | 10/1991 | Bourgeois | |

(Continued)

FOREIGN PATENT DOCUMENTS

DE    198 31 109    1/2000

(Continued)

OTHER PUBLICATIONS

M.T. Smith et al, "Presleep Cognitions in Patients with Insomnia Secondary to Chronic Pain", Journal of Behavioral Medicine, vol. 24, No. 1, 2001.

(Continued)

*Primary Examiner*—George R. Evanisko
*Assistant Examiner*—Rex Holmes
(74) *Attorney, Agent, or Firm*—Shumaker & Sieffert, P.A.

(57) ABSTRACT

A medical device delivers a therapy to a patient. The medical device may identify posture events, e.g., periodically determine a posture of the patient and/or identify posture transitions by the patient, and associate each determined posture event with a current therapy parameter set. A value of at least one posture metric is determined for each of a plurality of therapy parameter sets based on the posture events associated with that therapy parameter set. A list of the therapy parameter sets is presented to a user, such as a clinician, for evaluation of the relative efficacy of the therapy parameter sets. The list may be ordered according to the one or more posture metric values to aid in evaluation of the therapy parameter sets. Where values are determined for a plurality of posture metrics, the list may be ordered according to the one of the posture metrics selected by the user.

61 Claims, 7 Drawing Sheets

U.S. PATENT DOCUMENTS

| | | |
|---|---|---|
| 5,125,412 A | 6/1992 | Thornton |
| 5,154,180 A | 10/1992 | Blanchet et al. |
| 5,233,984 A | 8/1993 | Thompson |
| 5,275,159 A | 1/1994 | Griebel |
| 5,335,657 A | 8/1994 | Terry, Jr. et al. |
| 5,337,758 A | 8/1994 | Moore et al. |
| 5,342,409 A | 8/1994 | Mullett |
| 5,469,861 A | 11/1995 | Piscopo et al. |
| 5,476,483 A | 12/1995 | Bornzin et al. |
| 5,514,162 A | 5/1996 | Bornzin et al. |
| 5,593,431 A | 1/1997 | Sheldon |
| 5,622,428 A | 4/1997 | Bonnet |
| 5,645,053 A | 7/1997 | Remmers et al. |
| 5,732,696 A | 3/1998 | Rapoport et al. |
| 5,782,884 A | 7/1998 | Stotts et al. |
| 5,832,932 A | 11/1998 | Elsberry et al. |
| 5,895,371 A | 4/1999 | Levitas et al. |
| 5,904,708 A | 5/1999 | Goedeke |
| 5,919,149 A | 7/1999 | Allum |
| 5,941,906 A | 8/1999 | Barreras, Sr. et al. |
| 5,944,680 A | 8/1999 | Christopherson et al. |
| 6,044,297 A * | 3/2000 | Sheldon et al. ............... 607/17 |
| 6,045,513 A | 4/2000 | Stone et al. |
| 6,059,576 A | 5/2000 | Brann |
| 6,095,991 A | 8/2000 | Krausman et al. |
| 6,102,874 A | 8/2000 | Stone et al. |
| 6,120,467 A | 9/2000 | Schallhorn |
| 6,128,534 A | 10/2000 | Park et al. |
| 6,157,857 A | 12/2000 | Dimpfel |
| 6,165,143 A | 12/2000 | van Lummel |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,351,672 B1 | 2/2002 | Park et al. |
| 6,366,813 B1 | 4/2002 | DiLorenzo |
| 6,416,471 B1 | 7/2002 | Kumar et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,514,218 B2 | 2/2003 | Yamamoto |
| 6,539,249 B1 | 3/2003 | Kadhiresan et al. |
| 6,574,507 B1 | 6/2003 | Bonnet |
| 6,605,038 B1 | 8/2003 | Teller et al. |
| 6,611,783 B2 | 8/2003 | Kelly, Jr. et al. |
| 6,659,968 B1 | 12/2003 | McClure |
| 6,687,538 B1 | 2/2004 | Hrdlicka et al. |
| 6,731,984 B2 | 5/2004 | Cho et al. |
| 6,752,766 B2 | 6/2004 | Kowallik et al. |
| 6,773,404 B2 | 8/2004 | Poezevera et al. |
| 6,819,956 B2 | 11/2004 | DiLorenzo |
| 6,878,121 B2 | 4/2005 | Krausman et al. |
| 6,881,192 B1 | 4/2005 | Park |
| 6,884,596 B2 | 4/2005 | Civelli et al. |
| 6,890,306 B2 | 5/2005 | Poezevera |
| 6,928,324 B2 | 8/2005 | Park et al. |
| 6,964,641 B2 | 11/2005 | Cho et al. |
| 7,162,304 B1 | 1/2007 | Bradley |
| 7,209,787 B2 | 4/2007 | DiLorenzo |
| 2001/0037067 A1 | 11/2001 | Tchou et al. |
| 2002/0077562 A1 | 6/2002 | Kalgren et al. |
| 2002/0091308 A1 | 7/2002 | Kipshidze et al. |
| 2002/0161412 A1 | 10/2002 | Sun et al. |
| 2002/0169485 A1 | 11/2002 | Pless et al. |
| 2002/0177882 A1 | 11/2002 | DiLorenzo |
| 2002/0193697 A1 | 12/2002 | Cho et al. |
| 2002/0193839 A1 | 12/2002 | Cho et al. |
| 2003/0004423 A1 | 1/2003 | Lavie et al. |
| 2003/0139692 A1 | 7/2003 | Barrey et al. |
| 2003/0149457 A1 | 8/2003 | Tcheng et al. |
| 2003/0153953 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0171791 A1 | 9/2003 | KenKnight et al. |
| 2003/0212445 A1 | 11/2003 | Weinberg |
| 2004/0002741 A1 | 1/2004 | Weinberg |
| 2004/0002742 A1 | 1/2004 | Florio |
| 2004/0015103 A1 | 1/2004 | Aminian et al. |
| 2004/0049132 A1 | 3/2004 | Barron et al. |
| 2004/0102814 A1 | 5/2004 | Sorensen et al. |
| 2004/0111040 A1 | 6/2004 | Ni et al. |
| 2004/0111041 A1 | 6/2004 | Ni et al. |
| 2005/0021103 A1 | 1/2005 | DiLorenzo |
| 2005/0021104 A1 | 1/2005 | DiLorenzo |
| 2005/0042589 A1 | 2/2005 | Hatlestad et al. |
| 2005/0060001 A1 * | 3/2005 | Singhal et al. ............... 607/19 |
| 2005/0113710 A1 | 5/2005 | Stahmann et al. |
| 2005/0119703 A1 | 6/2005 | DiLorenzo |
| 2005/0177192 A1 | 8/2005 | Rezai et al. |
| 2005/0215847 A1 | 9/2005 | Heruth et al. |
| 2005/0222626 A1 | 10/2005 | DiLorenzo |
| 2005/0240086 A1 | 10/2005 | Akay |
| 2005/0240242 A1 | 10/2005 | DiLorenzo |
| 2005/0245790 A1 | 11/2005 | Bergfalk et al. |
| 2006/0224191 A1 | 10/2006 | DiLorenzo |
| 2006/0293720 A1 | 12/2006 | DiLorenzo |
| 2007/0073355 A1 | 3/2007 | DiLorenzo |
| 2007/0142862 A1 | 6/2007 | DiLorenzo |

FOREIGN PATENT DOCUMENTS

| | | |
|---|---|---|
| DE | 100 24 103 | 11/2001 |
| EP | 0 564 803 A1 | 10/1993 |
| EP | 0 849 715 B1 | 6/1998 |
| EP | 1 195 139 A1 | 4/2002 |
| EP | 1 291 036 A2 | 3/2003 |
| EP | 1 308 182 A2 | 5/2003 |
| EP | 1 437 159 A1 | 7/2004 |
| EP | 1 322 227 B1 | 12/2005 |
| GB | 2 330 912 | 5/1999 |
| WO | WO 98/00197 | 1/1998 |
| WO | WO 99/13765 | 3/1999 |
| WO | WO 01/37930 | 5/2001 |
| WO | WO 02/28282 | 4/2002 |
| WO | WO 02/28282 A1 | 4/2002 |
| WO | WO 02/41771 | 5/2002 |
| WO | WO 02/087433 | 11/2002 |
| WO | WO 02/096512 | 12/2002 |
| WO | WO 02/100267 | 12/2002 |
| WO | WO 02/100267 A1 | 12/2002 |
| WO | WO 03/024325 | 3/2003 |
| WO | WO 03/051356 | 6/2003 |
| WO | WO 03/051356 A1 | 6/2003 |
| WO | WO 03/065891 A2 | 8/2003 |
| WO | WO 2005/028029 | 3/2005 |
| WO | WO 2005/035050 | 4/2005 |

OTHER PUBLICATIONS

Michael T. Smith et al., "How do sleep disturbance and chronic pain inter-relate? Insights from the longitudinal and cognitive-behavioral clinical trials literature", Sleep Medicines Reviews, YSMRV 286-Jun. 19, 2003.

Suanne Goodrich et al., "The Predictions of Pain Using Measures of Sleep Quality", Pain Digest (1998) 8:23-25.

"Analysis of heart rate dynamics by methods derived from nonlinear mathematics: Clinical applicability and prognostic significance" http:/herkules.oulu.fi.isbn9514250133/html/x222.html (2004).

U.S. Patent Application entitled "Collecting Activity Information to Evaluate Therapy", U.S. Appl. No. 10/825,965, filed Apr. 15, 2004.

U.S. Patent Application entitled Collecting Sleep Quality Information via a Medical Device, U.S. Appl. No. 10/826,925, filed Apr. 15, 2004.

U.S. Patent Application entitled "Controlling Therapy Based on Sleep Quality" U.S. Appl. No. 10/825,953, filed Apr. 15, 2004.

U.S. Patent Application entitled "Collecting Activity and Sleep Quality Information via a Medical Device", U.S. Appl. No. 10/825,955, filed Apr. 15, 2004.

U.S. Patent Application entitled "Detecting Sleep", U.S. Appl. No. 10/825,964, filed Apr. 15, 2004.

U.S. Patent Application entitled "Sensitivity Analysis for Selecting Therapy Parameter Sets", U.S. Appl. No. 11/081,873, filed Mar. 16, 2005.

"Watch," Wikipedia, the free encyclopedia, 6 pgs., http://en.wikipedia.org/wiki/Watch, (2006).

"IBM & Citizen Watch develop Linux-based 'WatchPad'," 5 pgs., http://www.linuxdevices.com/news/NS6580187845.html, (2006).

Tuisku, Katinka, "Motor Activity Measured By Actometry in Neuropsychiatric Disorders," Department of Psychiatry, University of Helsinki, Helsinki, Finland, 115 pgs., (2002).

Kassam, M., "2005 EDP Topic 'MK4': Tremor Data-Logger for Parkinson's Disease Patients," http://www.ee.ryerson.ca/~courses/edp2005/MK4.html, 3 pgs., (2006).

"Design Competition: Runners-Up for the Best Three Designs," EPN, vol. 26, No. 1, (2002).

"MiniMitter® Physiological and Behavioral Monitoring for Humans and Animals," http://www.minimitter.com/Products/Actiwatch, 3 pgs., (2006).

International Search Report for corresponding PCT Application Serial No. PCT/US2005/008688, mailed Jun. 24, 2005 (4 pages).

Amzica, "Physiology of Sleep and Wakefulness as it Relates to the Physiology of Epilepsy," Journal of Clinical Neurophysiology, American Clinical Neurophysiology Society, 19(6), pp. 488-503, (2002).

Dinner, "Effect of Sleep on Epilepsy," Journal of Clinical Neurophysiology, American Clinical Neurophysiology Society, 19(6), pp. 504-513, (2002).

Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, (2002).

Mendez et al. "Interactions Between Sleep and Epilepsy," Journal of Clinical Neurophysiology, American Clinical Neurophysiology Society, 18(2), pp. 106-127, (2001).

Kerr et al., "Analysis of the sit-stand-sit movement cycle in normal subjects," Clinical Biomechanics, vol. 12, No. 4, pp. 236-245, (1997).

Aminian et al. "Physical Activity Monitoring Based on Accelerometry: Validation and Comparison with Video Observation," Medical & Biological Engineering & Computing, vol. 37, No. 2, pp. 304-308 (1999).

Medcare—A Global Leader in Sleep Diagnostics, Embletta Recording System, http://www.medcare.com/products/diagnostic/embletta/, 2 pgs. Jan. 31, 2005.

Medcare—A Global Leader in Sleep Diagnostics, Somnologica for Embletta, http://www.medcare.com/products/diagnostic/embletta/SomnoEmbletta/index.asp, 1 pg. Jan. 31, 2005.

MAP Medizin-Technologie GmbH, Poly-MESAM®, http://195.244.124.130/map/de/eng/map_med.nsf/cmsall/70564A3FCBE4188AC1256EF4.., 4 pgs. Jan. 31, 2005.

Merlin, http://www.aha.ru/~pir/english/merlin/, 4 pgs. Jan. 31, 2005.

Sleep Solutions—PR Newswire: Sleep Solutions Introduces NovaSom™ QSG™ for PSG . . . , http://www.sleep-solutions.com/press_room/novasom.htm, 2 pgs. Jan. 31, 2005.

Itamar Medical Information, http://itamar-medical.com/content.asp?id-id=31, 2 pgs. Jan. 31, 2005.

Criticare System Inc.,-504DX Portable Pulse Oximeter, http://www.csiusa.com/504dx.html, 4 pgs., Jan. 31, 2005.

Snap® Laboratories, Product Fact Sheet, http://www.snaplab.com/mp_fact.htm, 2 pgs. Jan. 31, 2005.

Sleep Strip & Bite Strip, http://www.quietsleep.com/snoringapnea/sleepstrip.htm, 8 pgs. Jan. 31, 2005.

"Bitestrip Flier," downloaded from Internet Archive of www.quietsleep.com dated Jan. 29, 2005 http://web.archive.org/web/20041124080003/www.quietsleep.com/pdf/Bitestrip+Flier.pdf.

"Bilateral Comparisons of the BiteStrip Bruxism Device and Masseter EMG Bruxism Events" downloaded from Internet Archive of www.quietsleep.com dated Jan. 29, 2005 http://web.archive.org/web/20041124075114/www.quietsleep.com/pdf/Bilateral+Comparisons.pdf.

"The BiteStrip: A Novel Screener for Sleep Bruxism," downloaded from Internet Archive of www.quietsleep.com dated Jan. 29, 2005 http://web.archive.org/web/20041124072922/www.quietsleep.com/pdf/BiteStrip-+Novel+Screener.pdf.

* cited by examiner

| PARAMETER SET | PARAMETERS | % UPRIGHT | TRANSITIONS/HOUR |
| --- | --- | --- | --- |
| 1 | PA = 5.5V<br>PW = 210ms<br>PR = 90Hz | 75% | 15 |
| 2 | PA = 5V<br>PW = 190ms<br>PR = 95Hz | 60% | 9 |
| ••• | | | |
| N | PA = 4.6V<br>PW = 215ms<br>PR = 80Hz | 55% | 8 |

FIG. 6

COLLECTING POSTURE INFORMATION TO EVALUATE THERAPY

This application claims the benefit of U.S. Provisional Application No. 60/553,784, filed Mar. 16, 2004, which is incorporated herein by reference in its entirety.

TECHNICAL FIELD

The invention relates to medical devices and, more particularly, to medical devices that deliver therapy.

BACKGROUND

In some cases, an ailment may affect a patient's activity level or range of activities by preventing the patient from being active. For example, chronic pain may cause a patient to avoid particular physical activities, or physical activity in general, where such activities increase the pain experienced by the patient. Other ailments that may affect patient activity include movement disorders and congestive heart failure. When a patient is inactive, he may be more likely to be recumbent, i.e., lying down, or sitting, and may change postures less frequently.

In some cases, these ailments are treated via a medical device, such as an implantable medical device (IMD). For example, patients may receive an implantable neurostimulator or drug delivery device to treat chronic pain or a movement disorder. Congestive heart failure may be treated by, for example, a cardiac pacemaker.

SUMMARY

In general, the invention is directed to techniques for evaluating a therapy delivered to a patient by a medical device based on posture information. At any given time, the medical device delivers the therapy according to a current set of therapy parameters. The therapy parameters may change over time such that the therapy is delivered according to a plurality of different therapy parameter sets. The medical device may identify posture events based on the posture of the patient, e.g., periodically identify the patient's posture and/or posture transitions, and associate each identified posture event with the current therapy parameter set. A value of at least one posture metric is determined for each of the therapy parameter sets based on the posture events associated with that parameter set. A list of the therapy parameter sets and associated posture metrics is presented to a user, such as clinician, for evaluation of the relative efficacy of the therapy parameter sets. The list may be ordered according to the posture metric values to aid in evaluation of the therapy parameter sets. In this manner, the user may readily identify the therapy parameter sets that support the highest activity levels for the patient, and evaluate the relative efficacy of the parameter sets.

The medical device monitors a plurality of signals that are generated by respective sensors and varies as a function of patient posture. For example, the medical device may monitor signals generated by a plurality of accelerometers, gyros, or magnetometers. The sensors may be oriented substantially orthogonally with each other, and each sensor may be substantially aligned with a body axis of the patient.

The medical device may identify a plurality of posture events based on the one or more signals. In some embodiments, the medical device periodically identifies the posture of the patient based on the one or more signals, and the identified posture is stored as a posture event. The medical device may identify whether the patient is upright or recumbent, e.g., lying down. In some embodiments in which sensors are located at a plurality of positions on or within the body of the patient, the medical device may be able to identify additional postures, such as standing, sitting and recumbent. Example locations for the sensors include on or with the trunk of the patient, e.g., within an implantable medical device in the abdomen of the patient, and additionally, in some embodiments, on or within an upper leg of the patient. In some embodiments, the medical device identifies transitions between postures, and stores indications of posture transitions as posture events.

As mentioned above, the medical device may associate each posture event with a current set of therapy parameters and, for each of a plurality of therapy parameter sets used by the medical device over time, a value of one or more posture metrics is determined. A posture metric value may be, for example, an amount or percentage of time spent in a posture while a therapy parameter set is active, e.g., average amount of time over a period of time, such as an hour, that a patient was within a particular posture. In some embodiments, a posture metric value may be an average number of posture transitions over a period of time, e.g., an hour, that a particular therapy parameter sets was active.

In embodiments in which a plurality of posture metrics are determined for each therapy parameter set, an overall posture metric may be determined based on the plurality of posture metrics. The plurality of posture metrics may be used as indices to select an overall posture metric from a look-up table comprising a scale of potential overall posture metrics. The scale may be numeric, such as overall posture metric values from 1-10.

The programming device or, in some external medical device embodiments, the medical device, presents a list of the plurality of parameter sets and associated posture metric values via a display. The programming device may order the list according to the posture metric values. Where values are determined for a plurality of posture metrics for each of the therapy parameter sets, the programming device may order the list according to the values of a user selected one of the posture metrics. The programming device may also present other posture information to a user, such as a trend diagram of identified postures over time, or a histogram or pie chart illustrating percentages of time that the patient assumed certain postures. The programming device may generate such charts or diagrams using posture events associated with a particular one of the therapy parameter sets, or all of the posture events identified by the medical device.

In one embodiment, the invention is directed to a method in which a plurality of signals are monitored, each of the signals generated by a respective one of a plurality of sensors as a function of posture of a patient. A plurality of posture events are identified based on the signals, and each of the posture events is associated with a therapy parameter set currently used by a medical device to deliver a therapy to the patient when the posture event is identified. A value of a posture metric is determined for each of a plurality of therapy parameter sets based posture events associated with the therapy parameter sets.

In another embodiment, the invention is directed to a medical system comprising a medical device that delivers a therapy to a patient, a plurality of sensors, and a processor. Each of the plurality of sensors generates a signal as a function of posture of the patient. The processor that monitors the plurality of signals generated by the sensors, identifies a plurality of posture events based on the signals, associates each of the posture events with a therapy parameter set currently used by the medical device to deliver a therapy to the patient when the posture event is identified, and determines a value of a posture metric for each of a plurality of therapy parameter sets based posture events associated with the therapy parameter sets.

In another embodiment, the invention is directed to a medical system comprising means for monitoring a plurality of signals, each of the signals generated by a respective one of a plurality of sensors as a function of posture of a patient, means for identifying a plurality of posture events based on the signals, means for associating each of the posture events with a therapy parameter set currently used by a medical device to deliver a therapy to the patient when the posture event is identified, and means for determining a value of a posture metric for each of a plurality of therapy parameter sets based posture events associated with the therapy parameter sets.

In another embodiment, the invention is directed to a medical system comprising an implantable medical device and an external programming device including a display. The implantable medical device delivers a therapy to a patient, monitors a plurality of signals, each of the signals generated by a respective one of a plurality of sensors as a function of posture of a patient, identifies a plurality of posture events based on the signals, and associates each of the posture events with a current therapy parameter set. The external programming receives information identifying a plurality of therapy parameter sets and associated posture events from the implantable medical device via telemetry, determines a value of a posture metric for each of a plurality of therapy parameter sets based on posture events associated with the therapy parameter sets, and presents a list of the plurality of therapy parameter sets and posture metric values associated with the therapy parameter sets via the display.

In another embodiment the invention is directed to a programming device comprising a telemetry circuit, a user interface including a display, and a processor. The processor receives information identifying a plurality of therapy parameter sets and associated posture events from an implantable medical device via the telemetry circuit, determines a value of a posture metric for each of a plurality of therapy parameter sets based on posture events associated with the therapy parameter sets, and presents a list of the plurality of therapy parameter sets and posture metric values associated with the therapy parameter sets via the display.

In another embodiment, the invention is directed to a computer-readable medium comprising program instructions. The program instructions cause a programmable processor to receive information identifying a plurality of therapy parameter sets and associated posture events from an implantable medical device, determine a value of posture metric for each of a plurality of therapy parameter sets based on activity levels associated with the therapy parameter sets, and present a list of the plurality of therapy parameter sets and posture metric values associated with the therapy parameter sets.

The invention is capable of providing one or more advantages. For example, a medical system according to the invention may provide a clinician with an objective indication of the efficacy of different sets of therapy parameters. Further, by displaying therapy parameter sets and associated posture metric values in an ordered and, in some cases, sortable list, the medical system may allow the clinician to more easily compare the relative efficacies of a plurality of therapy parameter sets. The medical system may be particularly useful in the context of trial neurostimulation for treatment of chronic pain, where the patient is encouraged to try a plurality of therapy parameter sets to allow the patient and clinician to identify efficacious therapy parameter sets.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 6 illustrates an example list of therapy parameter sets and associated activity metric values that may be presented by a clinician programmer.

DETAILED DESCRIPTION

Figure 1:
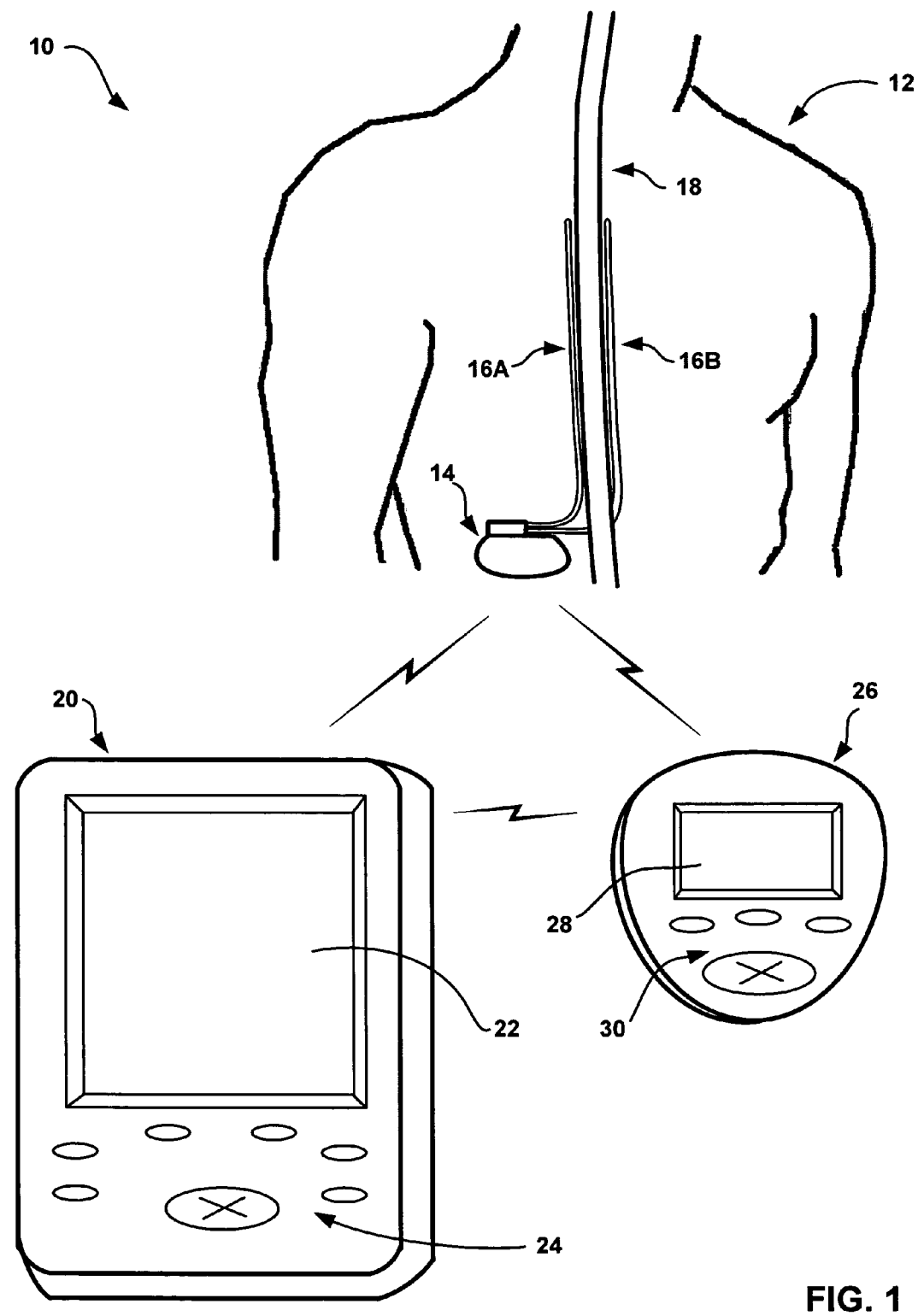
FIG. 1 is a conceptual diagram illustrating an example system that includes an implantable medical device that collects activity information according to the invention.

FIG. 1 is a conceptual diagram illustrating an example system 10 that includes an implantable medical device (IMD) 14 that collects information relating to the posture of a patient 12. In the illustrated example system 10, IMD 14 takes the form of an implantable neurostimulator that delivers neurostimulation therapy in the form of electrical pulses to patient 12. However, the invention is not limited to implementation via an implantable neurostimulator. For example, in some embodiments of the invention, IMD 14 may take the form of an implantable pump or implantable cardiac rhythm management device, such as a pacemaker, that collects posture information. Further, the invention is not limited to implementation via an IMD. In other words, any implantable or external medical device may collect activity information according to the invention.

In the illustrated example, IMD 14 delivers neurostimulation therapy to patient 12 via leads 16A and 16B (collectively "leads 16"). Leads 16 may, as shown in FIG. 1, be implanted proximate to the spinal cord 18 of patient 12, and IMD 14 may deliver spinal cord stimulation (SCS) therapy to patient 12 in order to, for example, reduce pain experienced by patient 12. However, the invention is not limited to the configuration of leads 16 shown in FIG. 1 or the delivery of SCS therapy. For example, one or more leads 16 may extend from IMD 14 to the brain (not shown) of patient 12, and MD 14 may deliver deep brain stimulation (DBS) therapy to patient 12 to, for example, treat tremor or epilepsy. As further examples, one or more leads 16 may be implanted proximate to the pelvic nerves (not shown) or stomach (not shown), and IMD 14 may deliver neurostimulation therapy to treat incontinence, sexual dysfunction, or gastroparesis.

IMD 14 delivers therapy according to a set of therapy parameters, i.e., a set of values for a number of parameters that define the therapy delivered according to that therapy parameter set. In embodiments where IMD 14 delivers neurostimulation therapy in the form of electrical pulses, the parameters of each parameter set may include voltage or current pulse amplitudes, pulse widths, pulse rates, duration, duty cycle, and the like. Further, each of leads 16 includes electrodes (not shown in FIG. 1), and a therapy parameter set may include information identifying which electrodes have been selected for delivery of pulses, and the polarities of the selected electrodes. Therapy parameter sets used by IMD 14 may include a number of parameter sets programmed by a clinician (not shown), and parameter sets representing adjustments made by patient 12 to these preprogrammed sets.

System 10 also includes a clinician programmer 20. The clinician may use clinician programmer 20 to program therapy for patient 12, e.g., specify a number of therapy parameter sets and provide the parameter sets to IMD 14. The clinician may also use clinician programmer 20 to retrieve information collected by IMD 14. The clinician may use clinician programmer 20 to communicate with IMD 14 both during initial programming of IMD 14, and for collection of information and further programming during follow-up visits.

Clinician programmer 20 may, as shown in FIG. 1, be a handheld computing device. Clinician programmer 20 includes a display 22, such as a LCD or LED display, to display information to a user. Clinician programmer 20 may also include a keypad 24, which may be used by a user to interact with clinician programmer 20. In some embodiments, display 22 may be a touch screen display, and a user may interact with clinician programmer 20 via display 22. A user may also interact with clinician programmer 20 using peripheral pointing devices, such as a stylus or mouse. Keypad 24 may take the form of an alphanumeric keypad or a reduced set of keys associated with particular functions.

System 10 also includes a patient programmer 26, which also may, as shown in FIG. 1, be a handheld computing device. Patient 12 may use patient programmer 26 to control the delivery of therapy by IMD 14. For example, using patient programmer 26, patient 12 may select a current therapy parameter set from among the therapy parameter sets preprogrammed by the clinician, or may adjust one or more parameters of a preprogrammed therapy parameter set to arrive at the current therapy parameter set.

Patient programmer 26 may include a display 28 and a keypad 30, to allow patient 12 to interact with patient programmer 26. In some embodiments, display 28 may be a touch screen display, and patient 12 may interact with patient programmer 26 via display 28. Patient 12 may also interact with patient programmer 26 using peripheral pointing devices, such as a stylus, mouse, or the like.

Clinician and patient programmers 20, 26 are not limited to the hand-held computer embodiments illustrated in FIG. 1. Programmers 20, 26 according to the invention may be any sort of computing device. For example, a programmer 20, 26 according to the invention may be a tablet-based computing device, a desktop computing device, or a workstation.

IMD 14, clinician programmer 20 and patient programmer 26 may, as shown in FIG. 1, communicate via wireless communication. Clinician programmer 20 and patient programmer 26 may, for example, communicate via wireless communication with IMD 14 using radio frequency (RF) telemetry or infrared techniques known in the art. Clinician programmer 20 and patient programmer 26 may communicate with each other using any of a variety of local wireless communication techniques, such as RF communication according to the 802.11 or Bluetooth specification sets, infrared communication according to the IRDA specification set, or other standard or proprietary telemetry protocols.

Clinician programmer 20 and patient programmer 26 need not communicate wirelessly, however. For example, programmers 20 and 26 may communicate via a wired connection, such as via a serial communication cable, or via exchange of removable media, such as magnetic or optical disks, or memory cards or sticks. Further, clinician programmer 20 may communicate with one or both of IMD 14 and patient programmer 26 via remote telemetry techniques known in the art, communicating via a local area network (LAN), wide area network (WAN), public switched telephone network (PSTN), or cellular telephone network, for example.

As mentioned above, IMD 14 collects patient posture information. Specifically, as will be described in greater detail below, IMD 14 may monitors a plurality of signals, each of the signal generated by a respective sensor as a function of patient posture, and may identify posture events based on the signals. IMD 14 may, for example, periodically identify the posture of patient 12 or transitions between postures made by patient 12 as posture events. For example, IMD 14 may identify whether the patient is upright or recumbent, e.g., lying down, whether the patient is standing, sitting, or recumbent, or transitions between such postures. IMD 14 may associate each determined posture event with the therapy parameter set that is currently active when the posture event is identified.

Over time, IMD 14 uses a plurality of therapy parameter sets to deliver the therapy to patient 12, and, as indicated above, may associate each identified posture event with a current set of therapy parameters. For each of a plurality of therapy parameter sets used by IMD 14 over time, a processor within IMD 14, clinician programmer 20, or patient programmer 26 may determine a value of one or more posture metrics based on the posture events associated with that therapy parameter set. A posture metric value may be, for example, an amount or percentage of time spent in a posture while a therapy parameter set is active, e.g., an average amount of time over a period of time, such as an hour, that patient 12 was within a particular posture. In some embodiments, a posture metric value may be an average number of posture transitions over a period of time, e.g., an hour.

In some embodiments, a plurality of posture metric values are determined for each of the plurality of therapy parameter sets. In such embodiments, an overall posture metric value may be determined. For example, the plurality of individual posture metric values may be used as indices to identify an overall posture metric value from a look-up table. The overall posture metric may selected from a predetermined scale of activity metric values, which may be numeric, such as activity metric values from 1-10.

One or more of IMD 14, clinician programmer 20, and patient programmer 26 may determine the posture metric values as described herein. In some embodiments, IMD 14 determines and stores posture metric values for each of a plurality of therapy parameter sets, and provides information identifying the therapy parameter sets and the associated posture metric values to, for example, programmer 20. In other embodiments, IMD 14 provides information identifying the therapy parameter sets and associated posture events to programmer 20, and the programmer determines the activity metric values for each of the therapy parameter sets using any of the techniques described herein with reference to IMD 14. In still other embodiments, IMD 14 provides signals output by sensors as function of patient posture to programmer 20, or the programmer receives the signals directed from the sensors via a wired or wireless link. In such embodiments, the programmer may identify posture events and determine posture metric values based on the signals using any of the techniques described herein with reference to IMD 14.

In any of these embodiments, programmer 20 may present a list of the plurality of parameter sets and associated posture metric values to the clinician via display 22. Programmer 20 may order the list according to the posture metric values. Where values are determined for a plurality of posture metrics for each of the therapy parameter sets, programmer 20 may order the list according to the values of one of the posture metrics that is selected by the clinician. Programmer 20 may also present other posture information to the clinician, such as a trend diagram of posture over time, or a histogram or pie chart illustrating percentages of time that the patient assumed certain postures. Programmer 20 may generate such charts or diagrams using posture events associated with a particular one of the therapy parameter sets, or all of the posture events identified over a period of time.

However, the invention is not limited to embodiments that include programmer 20, or embodiments in which programmer 20 presents posture information to the clinician. For example, in some embodiments, programmer 26 presents posture information as described herein to one or both of the clinician and patient 12. Further, in some embodiments, an external medical device comprises a display. In such embodiments, the external medical device both determines the activity metric values for the plurality of therapy parameter sets, and presents the list of therapy parameter sets and activity metric values.

Figure 2:
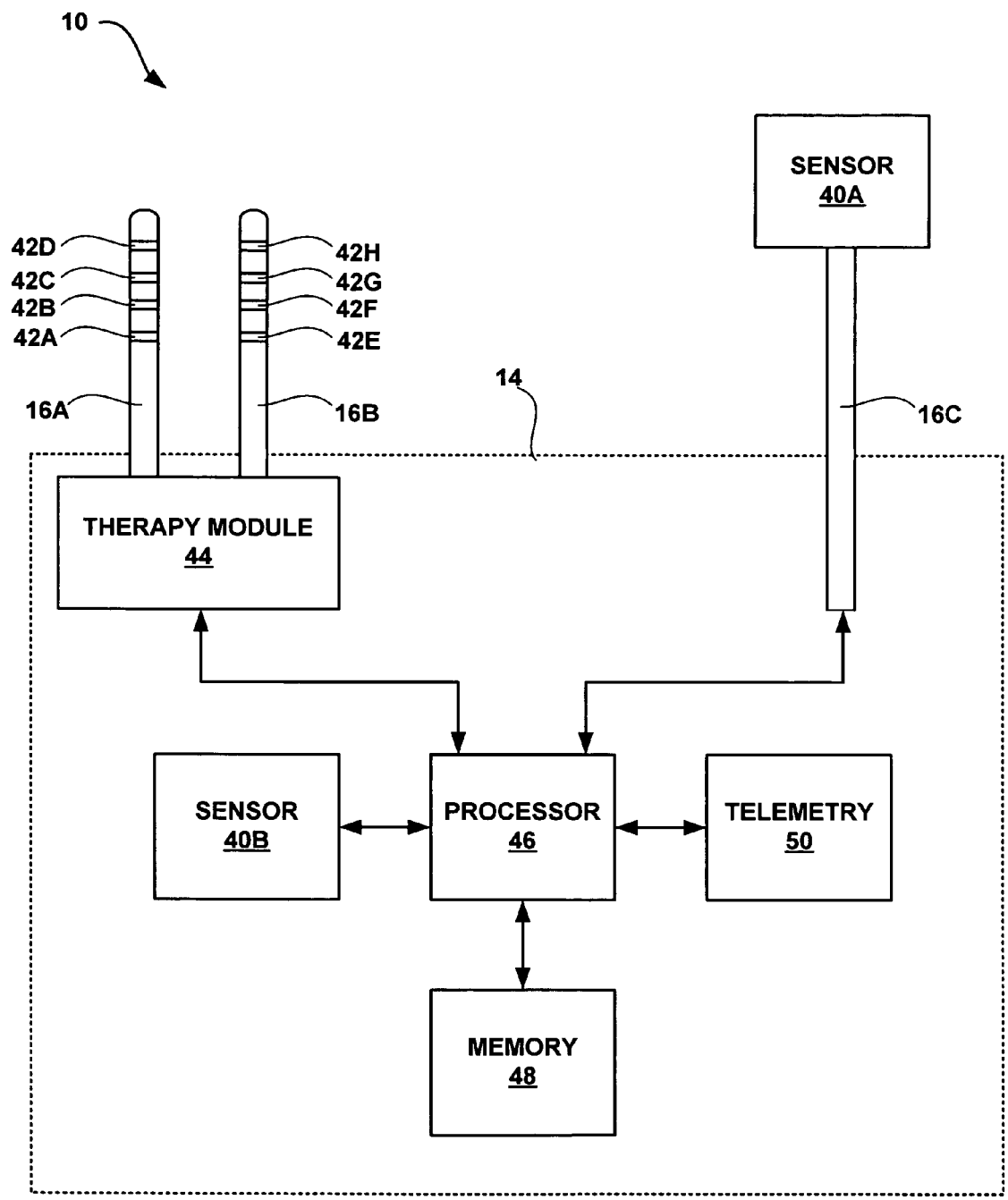
FIG. 2 is a block diagram further illustrating the example system and implantable medical device of FIG. 1.

FIG. 2 is a block diagram further illustrating system 10. In particular, FIG. 2 illustrates an example configuration of IMD 14 and leads 16A and 16B. FIG. 2 also illustrates sensors 40A and 40B (collectively "sensors 40") that generate signals that vary as a function of patient posture. As will be described in greater detail below, IMD 14 monitors the signals, and may identify posture events based on the signals.

IMD 14 may deliver neurostimulation therapy via electrodes 42A-D of lead 16A and electrodes 42E-H of lead 16B (collectively "electrodes 42"). Electrodes 42 may be ring electrodes. The configuration, type and number of electrodes 42 illustrated in FIG. 2 are merely exemplary. For example, leads 16A and 16B may each include eight electrodes 42, and the electrodes 42 need not be arranged linearly on each of leads 16A and 16B.

Electrodes 42 are electrically coupled to a therapy delivery module 44 via leads 16A and 16B. Therapy delivery module 44 may, for example, include an output pulse generator coupled to a power source such as a battery. Therapy delivery module 44 may deliver electrical pulses to patient 12 via at least some of electrodes 42 under the control of a processor 46, which controls therapy delivery module 44 to deliver neurostimulation therapy according to a current therapy parameter set. However, the invention is not limited to implantable neurostimulator embodiments or even to IMDs that deliver electrical stimulation. For example, in some embodiments a therapy delivery module 44 of an IMD may include a pump, circuitry to control the pump, and a reservoir to store a therapeutic agent for delivery via the pump.

Processor 46 may include a microprocessor, a controller, a digital signal processor (DSP), an application specific integrated circuit (ASIC), a field-programmable gate array (FPGA), discrete logic circuitry, or the like. Memory 48 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. In some embodiments, memory 48 stores program instructions that, when executed by processor 46, cause IMD 14 and processor 46 to perform the functions attributed to them herein.

Each of sensors 40 generates a signal that varies as a function of patient posture. IMD 14 may include circuitry (not shown) that conditions the signals generated by sensors 40 such that they may be analyzed by processor 46. For example, IMD 14 may include one or more analog to digital converters to convert analog signals generated by sensors 40 into digital signals usable by processor 46, as well as suitable filter and amplifier circuitry. Although shown as including two sensors 40, system 10 may include any number of sensors.

Further, as illustrated in FIG. 2, sensors 40 may be included as part of IMD 14, or coupled to IMD 14 via leads 16. Sensors 40 may be coupled to IMD 14 via therapy leads 16A and 16B, or via other leads 16, such as lead 16C depicted in FIG. 2. In some embodiments, a sensor 40 located outside of IMD 14 may be in wireless communication with processor 46.

Sensors 40 may include a plurality of accelerometers, gyros, or magnetometers that generate signals that indicate the posture of patient 12. Sensors 40 may be oriented substantially orthogonally with respect to each other. In addition to being oriented orthogonally with respect to each other, each of sensors 40 used to detect the posture of patient 12 may be substantially aligned with an axis of the body of patient 12. When accelerometers, for example, are aligned in this manner, the magnitude and polarity of DC components of the signals generate by the accelerometers indicate the orientation of the patient relative to the Earth's gravity, e.g., the posture of patient 12. Further information regarding use of orthogonally aligned accelerometers to determine patient posture may be found in a commonly assigned U.S. Pat. No. 5,593,431, which issued to Todd J. Sheldon.

Processor 46 may periodically determine the posture of patient 12, and may store indications of the determined postures within memory 48 as posture events. Where system 10 includes a plurality of orthogonally aligned sensors 40 located on or within the trunk of patient 12, e.g., within IMD 14 which is implanted within the abdomen of patient 12 as illustrated in FIG. 1, processor 46 may be able to periodically determine whether patient is, for example, upright or recumbent, e.g., lying down. In embodiments of system 10 that include an additional one or more sensors 40 at other locations on or within the body of patient 12, processor 46 may be able to identify additional postures of patient 12. For example, in an embodiment of system 10 that includes one or more sensors 40 located on or within the thigh of patient 12, processor 46 may be able to identify whether patient 12 is standing, sitting, or lying down. Processor 46 may also identify transitions between postures based on the signals output by sensors 40, and may store indications of the transitions, e.g., the time of transitions, as posture events within memory 48.

Processor 46 may identify postures and posture transitions by comparing the signals generated by sensors 40 to one or more respective threshold values. For example, when patient 12 is upright a DC component of the signal generated by one of a plurality of orthogonally aligned accelerometers may be substantially at a first value, e.g., high or one, while the DC components of the signals generated by others of the plurality of orthogonally aligned accelerometers may be substantially at a second value, e.g., low or zero. When patient 12 becomes recumbent, the DC component of the signal generated by one of the plurality of orthogonally aligned accelerometers that had been at the second value when the patient was upright may change to the first value, and the DC components of the signals generated by others of the plurality of orthogonally aligned accelerometers may remain at or change to the second value. Processor 46 may compare the signals generated by such sensors to respective threshold values to determine whether they are substantially at the first or second value, and to identify when the signals change from the first value to the second value.

Processor 46 may identify posture events continuously or periodically, e.g., one sample of the signals output by sensors 40 every minute or continuously for ten minutes each hour. In some embodiments, processor 46 limits recording of posture events to relevant time periods, i.e., when patient 12 is awake or likely to be awake, and therefore likely to be active. For example, patient 12 may indicate via patient programmer 26 when patient is going to sleep or awake. Processor 46 may receive these indications via a telemetry circuit 50 of IMD 14, and may suspend or resume recording of posture events based on the indications. In other embodiments, processor 46 may maintain a real-time clock, and may record posture events based on the time of day indicated by the clock, e.g., processor 46 may limit posture event recording to daytime hours.

In some embodiments, processor 46 may monitor one or more physiological parameters of patient 12 via signals generated by additional sensors 40, and may determine when patient 12 is attempting to sleep or asleep based on the physiological parameters. For example, processor 46 may determine when patient 12 is attempting to sleep by receiving an indication from patient programmer 26, monitoring a physiological parameter indicative of patient physical activity. In some embodiments, processor 46 may determine whether patient 12 is attempting to sleep by determining whether patient 12 remains in a recumbent posture for a threshold amount of time.

In other embodiments, processor 46 determines when patient 12 is attempting to fall asleep based on the level of melatonin in a bodily fluid. In such embodiments, a sensor 40 may take the form of a chemical sensor that is sensitive to the level of melatonin or a metabolite of melatonin in the bodily fluid, and estimate the time that patient 12 will attempt to fall asleep based on the detection. For example, processor 46 may compare the melatonin level or rate of change in the melatonin level to a threshold level stored in memory 48, and identify the time that threshold value is exceeded. Processor 46 may identify the time that patient 12 is attempting to fall asleep as the time that the threshold is exceeded, or some amount of time after the threshold is exceeded. Any of a variety of combinations or variations of the above-described techniques may be used to determine when patient 12 is attempting to fall asleep, and a specific one or more techniques may be selected based on the sleeping and activity habits of a particular patient.

In order to determine whether patient 12 is asleep, processor 46 may monitor any one or more physiological parameters that discernibly change when patient 12 falls asleep, such as activity level, posture, heart rate, respiration rate, respiratory volume, blood pressure, blood oxygen saturation, partial pressure of oxygen within blood, partial pressure of oxygen within cerebrospinal fluid, muscular activity, core temperature, arterial blood flow, and galvanic skin response. Processor 46 may additionally or alternatively monitor the variability of one or more of these physiological parameters, such as heart rate and respiration rate, which may discernible change when patient 12 is asleep. Further details regarding monitoring physiological parameters to identify when a patient is attempting to sleep and when the patient is asleep may be found in a commonly-assigned and co-pending U.S. patent application by Kenneth Heruth and Keith Miesel, entitled "DETECTING SLEEP," which was assigned U.S. patent application Ser. No. 10/825,964 and filed Apr. 15, 2004, and is incorporated herein by reference in its entirety.

In other embodiments, processor 46 may record posture events in response to receiving an indication from patient 12 via patient programmer 26. For example, processor 46 may record posture during times when patient 12 believes the therapy delivered by IMD 14 is ineffective and/or the symptoms experienced by patient 12 have worsened. In this manner, processor 46 may limit data collection to periods in which more probative data is likely to be collected, and thereby conserve a battery and/or storage space within memory 48.

Figure 3:
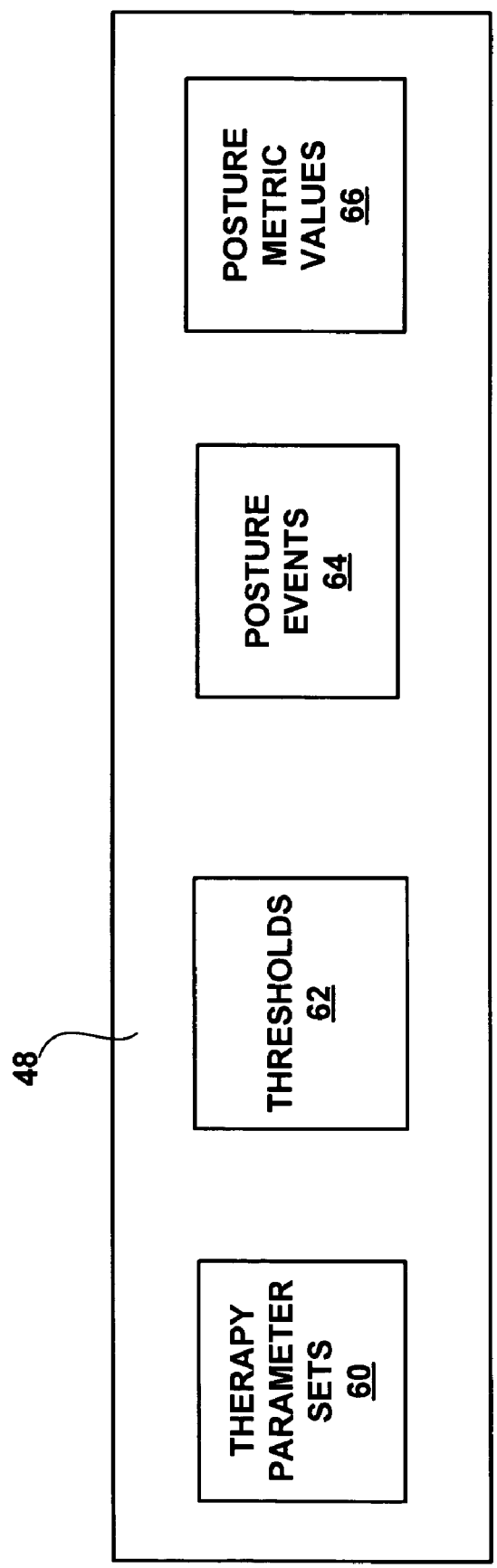
FIG. 3 is a block diagram illustrating an example memory of the implantable medical device of FIG. 1.

FIG. 3 illustrates memory 48 of IMD 14 in greater detail. As shown in FIG. 3, memory 48 stores information describing a plurality of therapy parameter sets 60. Therapy parameter sets 60 may include parameter sets specified by a clinician using clinician programmer 20. Therapy parameter sets 60 may also include parameter sets that are the result of patient 12 changing one or more parameters of one of the preprogrammed therapy parameter sets. For example, patient 12 may change parameters such as pulse amplitude, pulse frequency, or pulse width via patient programmer 26.

Memory 48 also stores thresholds 62 used by processor 46 to identify postures of patient 12 and/or transitions between postures, as discussed above. When processor 46 identifies a posture event 64 as discussed above, processor 46 associates the posture event 64 with the current one of therapy parameter sets 60, e.g., the one of therapy parameter sets 60 that processor 46 is currently using to control delivery of therapy by therapy module 44 to patient 12. For example, processor 46 may store determined posture event 64 within memory 48 with an indication of the parameter sets 60 with which they are associated. In other embodiments, processor 46 stores samples (not shown) of signals generated by sensors 40 within memory 48 with an indication of the parameter sets 60 with which they are associated.

In some embodiments, processor 46 determines a value of one or more posture metrics for each of therapy parameter sets 60 based on the posture events 63 associated with the parameter sets 60. Processor 46 may store the determined posture metric values 66 within memory 48 with an indication as to which of therapy parameter sets 60 the determined values are associated with. For example, processor 46 may determine an amount of time that patient 12 was in a posture when a therapy parameter set 60 was active, e.g., an average amount of time over a period of time such as an hour, as a posture metric 66 for the therapy parameter set 60. Processor 46 may additionally or alternatively determine percentages of time that patient 12 assumed one or more postures while a therapy parameter set was active as a posture metric 66 for the therapy parameter set 60. As another example, processor 46 may determine an average number of transitions over a period of time, such as an hour, when a therapy parameter set 60 was active as a posture metric 66 for the therapy parameter set 60.

In some embodiments, processor 46 determines a plurality of posture metric values 66 for each of the plurality of therapy parameter sets 60, and determines an overall posture metric value 66 for a parameter set based on the values of the individual posture metrics for that parameter set. For example, processor 46 may use the plurality of individual posture metric values as indices to identify an overall posture metric value from a look-up table stored in memory 48. Processor 46 may select the overall posture metric value from a predetermined scale of posture metric values, which may be numeric, such as posture metric values from 1-10.

As shown in FIG. 2, IMD 14 includes a telemetry circuit 50, and processor 46 communicates with programmers 20, 26 via telemetry circuit 50. In some embodiments, processor 46 provides information identifying therapy parameter sets 60 and posture metric values 66 associated with the parameter sets to programmer 20, and programmer 20 displays a list of therapy parameter sets 60 and associated activity metric values 66. In other embodiments, as will be described in greater detail below, processor 46 does not determine posture metric values 66. Instead, processor 46 provides information describing posture events 64 to programmer 20 via telemetry circuit 50, and programmer 20 determines posture metric values 66 for display to the clinician. Further, in other embodiments, processor 46 provides samples of signals generated by sensors 40 to programmer 20 via telemetry circuit 50, and programmer 20 may both identify posture events 64 and determine posture metric values 66 based on the samples. In still other embodiments, one of programmers 20, 26 receives one or more of the signals generated by sensors 40 directly, and the programmer may both identify posture events 64 and determine posture metric values 66 based on the signals. Some external medical device embodiments of the invention include a display, and a processor of such an external medical device may both determine posture metric values 66 and display a list of therapy parameter sets 60 and associated posture metric values 66 to a clinician.

Figure 4:
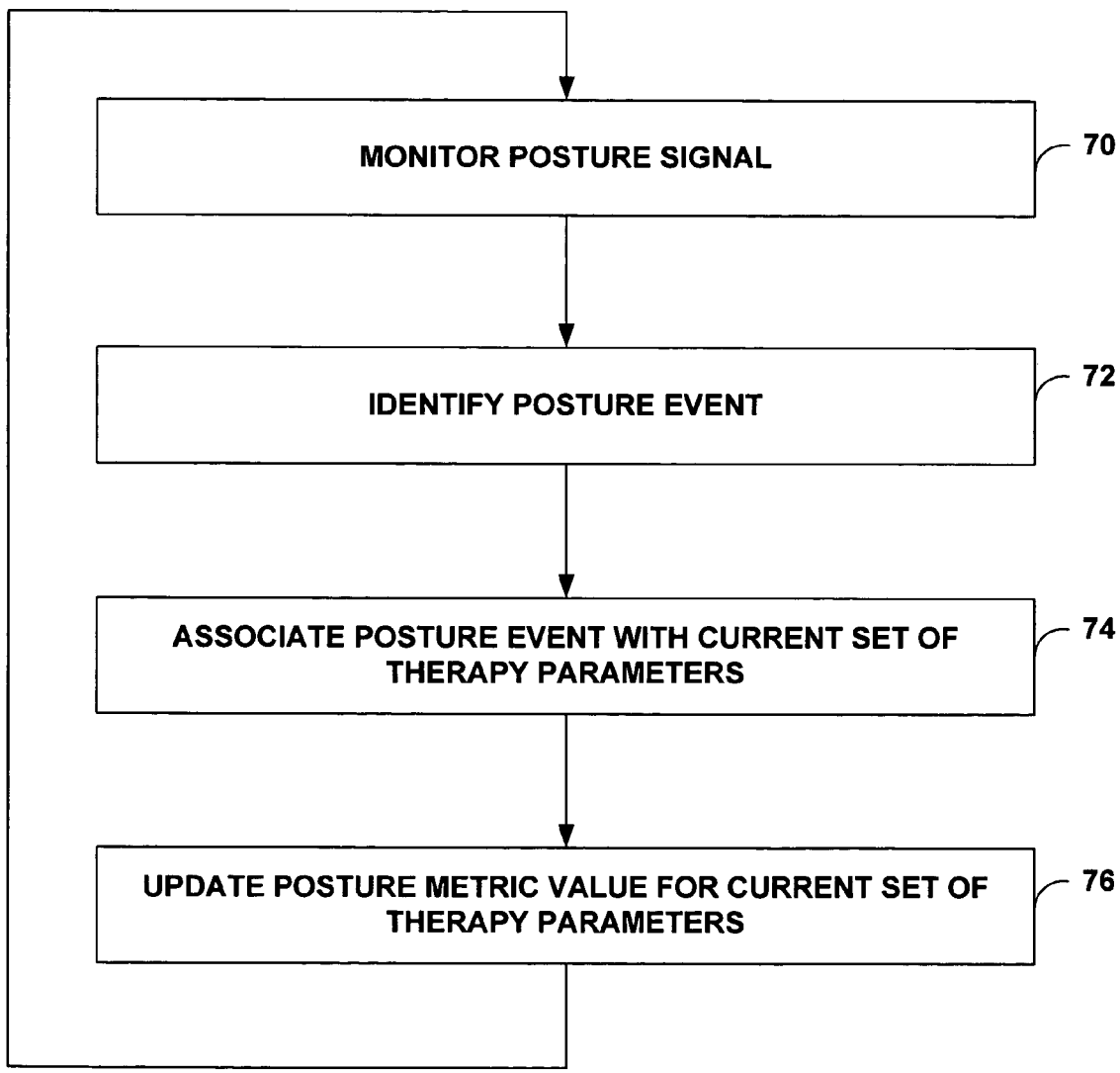
FIG. 4 is a flow diagram illustrating an example method for collecting activity information that may be employed by an implantable medical device.

FIG. 4 is a flow diagram illustrating an example method for collecting posture information that may be employed by IMD 14. IMD 14 monitors a plurality of signals generated by sensors 40 as a function of the posture of patient 12 (70). For example, IMD 14 may monitor the DC components of signals generated by a plurality of substantially orthogonally aligned accelerometers. Each of the accelerometers may be substantially aligned with a respective axis of the body of patient 12.

IMD 14 identifies a posture event 64 (72). For example, IMD 14 may identify a current posture of patient 12 at a time when the signals generated by sensors 40 are sampled, or may identify the occurrence of a transition between postures. IMD 14 identifies the current therapy parameter set 60, and associates the identified posture event 64 with the current therapy parameter set 60 (74). For example, IMD 14 may store information describing the identified posture event 64 within memory 48 with an indication of the current therapy parameter set 60. IMD 14 may then update one or more posture metric values 66 associated with the current therapy parameter set 60, as described above (76).

IMD 14 may periodically perform the example method illustrated in FIG. 4, e.g., may periodically monitor the posture signals (70), identify posture events 64 (72), and associate the identified posture events 64 with a current therapy parameter set 60 (74). As described above, IMD 14 may only perform the example method during daytime hours, or when patient is awake and not attempting to sleep, and/or only in response to an indication received from patient 12 via patient programmer 26. IMD 14 need not update posture metric values 66 each time a posture event 64 is identified, e.g., each time the posture signals are sampled to identify the posture of patient 12. In some embodiments, for example, IMD 14 may store posture events 64 within memory, and may determine the posture metric values 66 upon receiving a request for the values from clinician programmer 20.

Further, in some embodiments, as will be described in greater detail below, IMD 14 does not determine the posture metric values 66, but instead provides information describing posture events 64 to a programming device, such as clinician programmer 20 or patient programmer 26. In such embodiments, the programming device determines the posture metric values 66 associated with each of the therapy parameter sets 60. Additionally, as described above, IMD 14 need not identify posture events 64. Instead, a programming device may receive posture signals from IMD 14 or directly from sensors 40, and may both identify posture events 64 and determine posture metric values 66 based on the samples.

Figure 5:
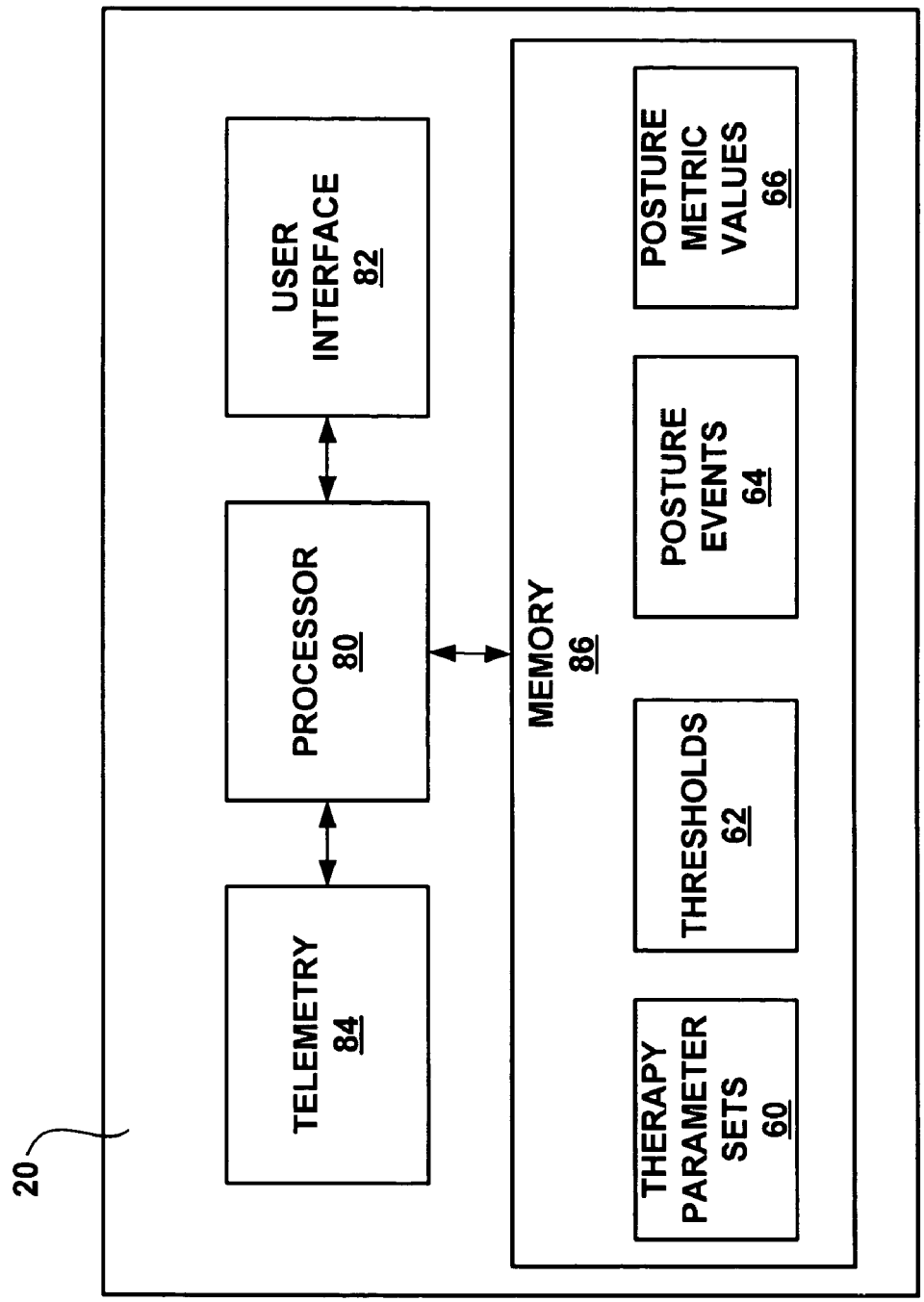
FIG. 5 is a block diagram illustrating an example clinician programmer.

FIG. 5 is a block diagram illustrating clinician programmer 20. A clinician may interact with a processor 80 via a user interface 82 in order to program therapy for patient 12, e.g., specify therapy parameter sets. Processor 80 may provide the specified therapy parameter sets to IMD 14 via telemetry circuit 84.

At another time, e.g., during a follow up visit, processor 80 may receive information identifying a plurality of therapy parameter sets 60 from IMD 14 via telemetry circuit 84, which may be stored in a memory 86. The therapy parameter sets 60 may include the originally specified parameter sets, and parameter sets resulting from manipulation of one or more therapy parameters by patient 12 using patient programmer 26. In some embodiments, processor 80 also receives posture metric values 66 associated with the therapy parameter sets 60, and stores the posture metric values 66 in memory 86.

In other embodiments, processor 80 receives information describing posture events 64 associated with the therapy parameter sets 60, and determines values 66 of one or more posture metrics for each of the plurality of therapy parameter sets 60 using any of the techniques described above with reference to IMD 14 and FIGS. 2 and 3. In still other embodiments, processor 80 receives the samples of the signals output by sensors 40 from IMD 14, or directly from sensors 40, and identifies posture events 64 and determines posture metric values 66 based on signals using any of the techniques described above with reference to MD 14 and FIGS. 2 and 3.

Upon receiving or determining posture metric values 66, processor 80 generates a list of the therapy parameter sets 60 and associated posture metric values 66, and presents the list to the clinician. User interface 82 may include display 22, and processor 80 may display the list via display 22. The list of therapy parameter sets 60 may be ordered according to the associated posture metric values 66. Where a plurality of posture metric values are associated with each of the parameter sets, the list may be ordered according to the values of the posture metric selected by the clinician. Processor 80 may also present other posture information to a user, such as a trend diagram of posture over time, or a histogram, pie chart, or other illustration of percentages of time that patient 12 assumed certain postures. Processor 80 may generate such charts or diagrams using posture events 64 associated with a particular one of the therapy parameter sets 60, or all of the posture events recorded by IMD 14.

User interface 82 may include display 22 and keypad 24, and may also include a touch screen or peripheral pointing devices as described above. Processor 80 may include a microprocessor, a controller, a DSP, an ASIC, an FPGA, discrete logic circuitry, or the like. Memory 86 may include program instructions that, when executed by processor 80, cause clinician programmer 20 to perform the functions ascribed to clinician programmer 20 herein. Memory 86 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

FIG. 6 illustrates an example list 90 of therapy parameter sets and associated posture metric values 66 that may be presented by clinician programmer 20. Each row of example list 130 includes an identification of one of therapy parameter sets 60, the parameters of the therapy parameter set, and values 66 associated with the therapy parameter set for each of two illustrated posture metrics. Programmer 20 may order list 90 according to a user-selected one of the posture metrics.

The posture metrics illustrated in FIG. 6 are a percentage of time upright, and an average number of posture transitions per hour. IMD 14 or programmer 20 may determine the average number of posture transitions per hour for one of the illustrated therapy parameter sets by identifying the total number of posture transitions associated with the parameter set and the total amount of time that IMD 14 was using the parameter set. IMD 14 or programmer 20 may determine the percentage of time upright for one of parameter sets 60 as the percentage of the total time that the therapy parameter set was in use that patient 12 was identified to be in an upright position.

Figure 7:
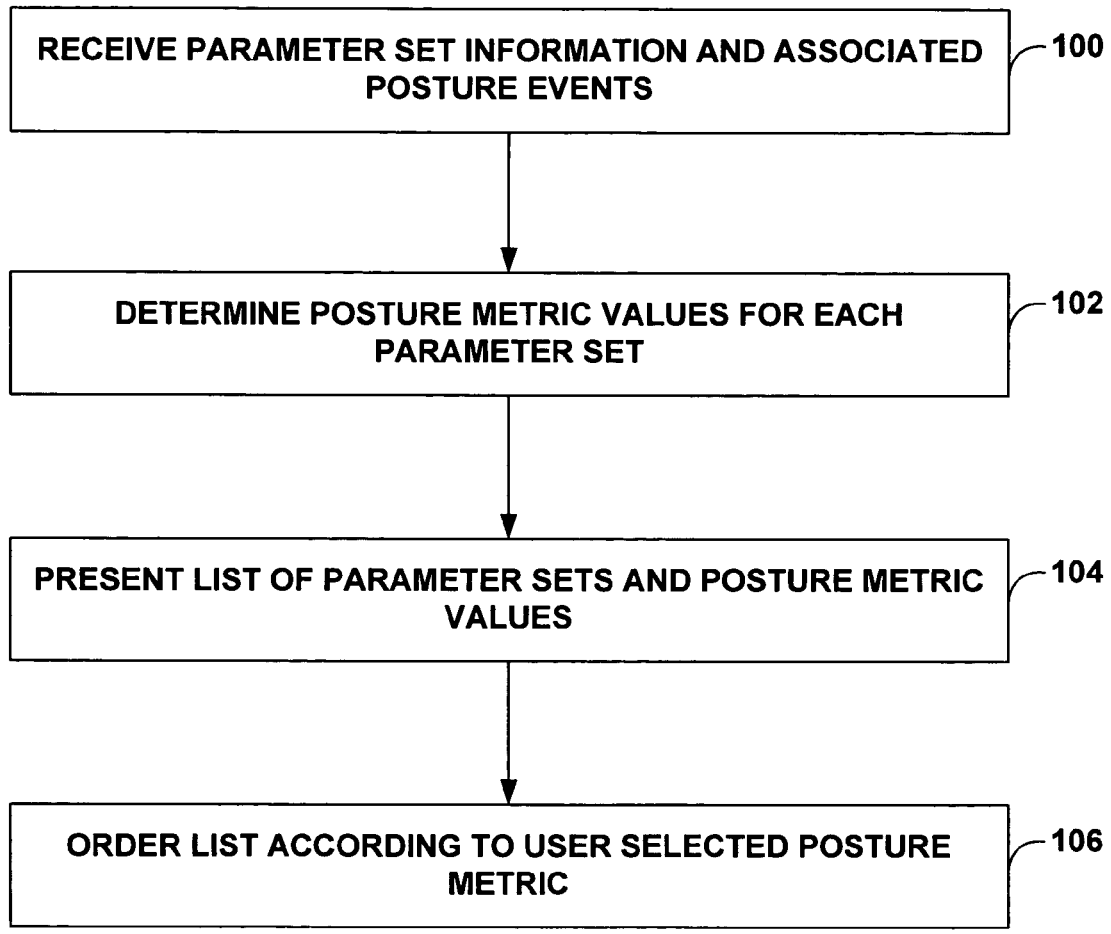
FIG. 7 is a flow diagram illustrating an example method for displaying a list of therapy parameter sets and associated activity metric values that may be employed by a clinician programmer.

FIG. 7 is a flow diagram illustrating an example method for displaying a list of therapy parameter sets 60 and associated posture metric values 66 that may be employed by a clinician programmer 20. Programmer 20 receives information identifying therapy parameter sets 60 and associated posture events from IMD 14 (100). Programmer 20 then determines one or more posture metric values 66 for each of the therapy parameter sets based on the posture events 64 associated with the therapy parameter sets (102). In embodiments in which programmer 20 determines posture metric values 66, the clinician may be able to specify which of a plurality of possible posture metric values 66 are determined. In other embodiments, IMD 14 determines the posture metric values 66, and provides them to programmer 20, or provides samples of posture signals associated with therapy parameter sets to programmer 20 for determination of posture metric values, as described above. After receiving or determining posture metric values 66, programmer 20 presents a list 90 of therapy parameter sets 60 and associated posture metric values 66 to the clinician, e.g., via display 22 (104). Programmer 20 may order list 90 of therapy parameter sets 60 according to the associated posture metric values 66, and the clinician may select the posture metric that list 90 is ordered according to via a user interface 82 (106).

Various embodiments of the invention have been described. However, one skilled in the art will recognize that various modifications may be made to the described embodiments without departing from the scope of the invention. For example, although described herein primarily in the context of treatment of pain with an implantable neurostimulator, the invention is not so limited. The invention may be embodied in any implantable medical device that delivers a therapy, such as a cardiac pacemaker or an implantable pump. Further, the invention may be implemented via an external, e.g., non-implantable, medical device. In such embodiments, the external medical device itself may include a user interface and display to present posture information to a user, such as a clinician or patient, for evaluation of therapy parameter sets.

As another example, the invention may be embodied in a trial neurostimulator, which is coupled to percutaneous leads implanted within the patient to determine whether the patient is a candidate for neurostimulation, and to evaluate prospective neurostimulation therapy parameter sets. Similarly, the invention may be embodied in a trial drug pump, which is coupled to a percutaneous catheter implanted within the patient to determine whether the patient is a candidate for an implantable pump, and to evaluate prospective therapeutic agent delivery parameter sets. Posture metric values collected by the trial neurostimulator or pump may be used by a clinician to evaluate the prospective therapy parameter sets, and select parameter sets for use by the later implanted non-trial neurostimulator or pump. In particular, a trial neurostimulator or pump may determine values of one or more posture metrics for each of a plurality of prospective therapy parameter sets, and a clinician programmer may present a list of prospective parameter sets and associated posture metric values to a clinician. The clinician may use the list to identify potentially efficacious parameter sets, and may program a permanent implantable neurostimulator or pump for the patient with the identified parameter sets.

Further, the invention may be embodied as a computer-readable medium that includes instructions to cause a processor to perform any of the methods described herein. These and other embodiments are within the scope of the following claims.

The invention claimed is:

1. A method comprising:
monitoring a plurality of signals, each of the signals generated by a respective one of a plurality of sensors as a function of posture of a patient;
identifying a plurality of posture events based on the signals;
associating each of the posture events with a therapy parameter set that was used by a medical device to deliver a therapy to the patient when the posture event was identified; and
for each of the plurality of therapy parameter sets, determining a value of a posture metric based on the posture events associated with the therapy parameter set, the value of the posture metric indicating an efficacy of the therapy parameter set.

2. The method of claim 1, wherein the plurality of sensors comprises a plurality of orthogonally aligned accelerometers, and identifying a plurality of posture events comprises identifying a plurality of posture events based on a DC component of each of the signals generated by the plurality of accelerometers.

3. The method of claim 1, wherein the plurality of sensors are positioned at a plurality of locations, each of locations one of on and within a body of the patient.

4. The method of claim 1, wherein identifying a plurality of posture events comprises periodically identifying a posture of the patient.

5. The method of claim 4, wherein periodically identifying a posture comprises periodically identifying whether the patient is upright or recumbent.

6. The method of claim 4, wherein periodically identifying a posture comprises periodically identifying whether the patient is standing, sitting, or recumbent.

7. The method of claim 4, wherein periodically identifying a posture comprises comparing at least one of the signals to at least one threshold value.

8. The method of claim 4, wherein determining a value of a posture metric for a therapy parameter set comprises determining at least one of an amount and a percentage of time spent in a posture based on the determined postures associated with the therapy parameter set.

9. The method of claim 1, wherein identifying a plurality of posture events comprises identifying posture transitions.

10. The method of claim 9, wherein determining a value of a posture metric for a therapy parameter set comprises determining an average number of posture transitions over a period of time based on the identified posture transitions associated with the parameter set.

11. The method of claim 1, wherein identifying a plurality of posture events comprises:
determining when the patient is awake; and
identifying posture events while the patient is awake.

12. The method of claim 1, further comprising presenting a list of the plurality of therapy parameter sets and posture metric values associated with the therapy parameter sets.

13. The method of claim 12, further comprising ordering the list of therapy parameter sets according to the associated posture metric values.

14. The method of claim 13, wherein determining a value of a posture metric comprises determining a value of each of a plurality of posture metrics for each of a plurality of therapy parameter sets based on posture events associated with the therapy parameter sets, and ordering the list comprises ordering the list according to a user selected one of the posture metrics.

15. The method of claim 1, wherein determining a value of a posture metric comprises:
determining a value of each of a plurality of posture metrics; and
determining a value of an overall posture metric based on the plurality of posture metric values.

16. The method of claim 1, further comprising presenting a graphical representation of the identified posture events.

17. The method of claim 16, wherein presenting a graphical representation comprises presenting at least one of a trend diagram, a histogram and a pie chart based on the identified posture events.

18. The method of claim 1, wherein the medical device comprises an implantable medical device.

19. The method of claim 18, wherein the implantable medical device comprises at least one of an implantable neurostimulator and an implantable drug pump.

20. The method of claim 1, wherein the medical device comprises at least one of a trial neurostimulator and a trial pump.

21. A medical system comprising:
a medical device that delivers a therapy to a patient;
a plurality of sensors, each of the sensors generating a signal as a function of posture of the patient; and
a processor that monitors the plurality of signals generated by the sensors, identifies a plurality of posture events based on the signals, associates each of the posture events with a therapy parameter set that was used by the medical device to deliver a therapy to the patient when the posture event was identified, and, for each of the plurality of therapy parameter sets, determines a value of a posture metric based on the posture events associated with the therapy parameter set, the value of the posture metric indicating an efficacy of the therapy parameter set.

22. The medical system of claim 21, wherein the plurality of sensors comprises a plurality of orthogonally aligned accelerometers, and the processor identifies the plurality of posture events based on a DC component of each of the signals generated by the plurality of accelerometers.

23. The medical system of claim 21, wherein the plurality of sensors are positioned at a plurality of locations, each of locations one of on and within a body of the patient.

24. The medical system of claim 21, wherein medical device includes at least some of the sensors.

25. The medical system of claim 21, wherein the processor periodically identifies a posture of the patient based on the signals.

26. The medical system of claim 25, wherein the processor periodically identifies whether the patient is upright or recumbent based on the signals.

27. The medical system of claim 25, wherein the processor periodically identifies whether the patient is standing, sitting, or recumbent based on the signals.

28. The medical system of claim 25, wherein processor compares at least one of the signals to at least one threshold value, and periodically identifies a posture based on the comparison.

29. The medical system of claim 25, wherein the processor determines at least one of an amount and a percentage of time spent in a posture based on the determined postures associated with a therapy parameter set as a value of a posture metric for the therapy parameter set.

30. The medical system of claim 21, wherein the processor identifies posture transitions as posture events.

31. The medical system of claim 30, wherein the processor determines an average number of posture transitions over a period of time as a value of a posture metric for a therapy parameter set based on the identified posture transitions associated with the parameter set.

32. The medical system of claim 21, wherein the processor determines when the patient is awake, and identifies posture events while the patient is awake.

33. The medical system of claim 21, further comprising a display that presents a list of the plurality of therapy parameter sets and posture metric values associated with the therapy parameter sets.

34. The medical system of claim 33, further comprising a programming device that includes the display, wherein the programming device orders the list of therapy parameter sets according to the associated posture metric values.

35. The medical system of claim 34, wherein the processor determines a value of each of a plurality of posture metrics for each of a plurality of therapy parameter sets based on posture events associated with the therapy parameter sets, and the programming device orders the list according to a user selected one of the posture metrics.

36. The medical system of claim 21, wherein the processor determines a value of each of a plurality of posture metrics, and determines a value of an overall posture metric based on the plurality of posture metric values.

37. The medical system of claim 21, further comprising a programming device that includes the display, wherein the programming device presents a graphical representation of the identified posture events via the display.

38. The medical system of claim 37, wherein the programming device presents at least one of a trend diagram, a histogram and a pie chart based on the identified posture events.

39. The medical system of claim 21, wherein the medical device comprises an implantable medical device.

40. The medical system of claim 39, wherein the implantable medical device comprises at least one of an implantable neurostimulator and an implantable drug pump.

41. The medical system of claim 21, wherein the medical device comprises at least one of a trial neurostimulator and a trial pump.

42. The medical system of claim 21, wherein the processor comprises a processor of the medical device.

43. The medical system of claim 21, further comprising a programming device, wherein the processor comprises a processor of the programming device.

44. A medical system comprising:
means for monitoring a plurality of signals, each of the signals generated by a respective one of a plurality of sensors as a function of posture of a patient;
means for identifying a plurality of posture events based on the signals;
means for associating each of the posture events with a therapy parameter set that was used by a medical device to deliver a therapy to the patient when the posture event was identified; and
means for determining, for each of the therapy parameter sets, a value of a posture metric based on the posture events associated with the therapy parameter set, the value of the posture metric indicating an efficacy of the therapy parameter set.

45. The medical system of claim 44, further comprising means for presenting a list of the plurality of therapy parameter sets and posture metric values associated with the therapy parameter sets.

46. The medical system of claim 45, further comprising means for ordering the list according to the posture metric values.

47. The medical system of claim 46, further comprising means for determining a value of each of a plurality of posture metrics for each of a plurality of therapy parameter sets based on posture events associated with the therapy parameter sets, wherein the means for ordering the list comprises means for ordering the list according to a user selected one of the posture metrics.

48. A medical system comprising:
an implantable medical device that that delivers a therapy to a patient, monitors a plurality of signals, each of the signals generated by a respective one of a plurality of sensors as a function of posture of a patient, identifies a plurality of posture events based on the signals, and associates each of the posture events with a therapy parameter set that was used to control delivery of the therapy when the posture event was identified; and
an external programming device that:
includes a display,
receives information identifying a plurality of therapy parameter sets and
associated posture events from the implantable medical device via telemetry,
determines, for each of a plurality of therapy parameter sets, a value of a posture metric based on the posture events associated with the therapy parameter set, the value of the posture metric indicating an efficacy of the therapy parameter set, and
presents a list of the plurality of therapy parameter sets and posture metric values associated with the therapy parameter sets via the display for comparison of the efficacies of the plurality of therapy parameter sets.

49. The medical system of claim 48, wherein the implantable medical device determines when the patient is awake, and identifies posture events while the patient is awake.

50. The medical system of claim 49,
wherein the implantable medical device periodically identifies postures as posture events, and
wherein, for each of the therapy parameter sets, the external programming device determines at least one of an amount and a percentage of time spent in a posture based on the determined postures associated with a therapy parameter set as a value of a posture metric for the therapy parameter set.

51. The medical system of claim 48,
wherein the implantable medical device identifies posture transitions as posture events, and
wherein, for each of the therapy parameter sets, the external programming device determines an average number of posture transitions over a period of time as a value of a posture metric for a therapy parameter set based on the identified posture transitions associated with the parameter set.

52. The medical system of claim 48, wherein the programming device orders the list of therapy parameter sets according to the associated posture metric values.

53. The medical system of claim 52, wherein the programming device determines a value of each of a plurality of posture metrics for each of the plurality of therapy parameter sets based on posture events associated with the therapy parameter sets, receives a selection of one of the posture metrics from a user, and orders the list according to the user selected one of the posture metrics.

54. The medical system of claim 48, wherein the implantable medical device comprises at least one of an implantable neurostimulator and an implantable drug pump.

55. The medical system of claim 48,
further comprising the plurality sensors,
wherein sensors comprise a plurality of accelerometers, and the implantable medical device identifies a plurality of posture events based on a DC component of each of the signals generated by the plurality of accelerometers.

56. The medical system of claim 55, wherein at least some of the sensor are included within the implantable medical device.

57. The medical system of claim 56, wherein the sensors are located a plurality of locations, each of the locations one of on and within a body of the patient.

58. A programming device comprising:
a telemetry circuit;
a user interface including a display; and
a processor that receives information identifying a plurality of therapy parameter sets and associated posture events from an implantable medical device via the telemetry circuit, determines, for each of a plurality of therapy parameter sets, a value of a posture metric based on the posture events associated with the therapy parameter set, the value of the posture metric indicating an efficacy of the therapy parameter set, and presents a list of the plurality of therapy parameter sets and posture metric values associated with the therapy parameter sets via the display for comparison of the efficacies of the plurality of therapy parameter sets.

59. The programming device of claim 58, wherein the processor orders the list of therapy parameter sets according to the associated posture metric values.

60. The programming device of claim 59, wherein the processor determines a value of each of a plurality of posture metrics for each of the plurality of therapy parameter sets based on posture events associated with the therapy parameter sets, receives a selection of one of the posture metrics from a user via the user interface, and orders the list according to the user selected one of the posture metrics.

61. A computer-readable medium comprising instructions that cause a programmable processor to:
receive information identifying a plurality of therapy parameter sets and associated posture events from an implantable medical device;
for each of a plurality of therapy parameter sets, determine a value of posture metric based on the posture events associated with the therapy parameter set, the value of the posture metric indicatin an efficacy of the therapy parameter set; and
present a list of the plurality of therapy parameter sets and posture metric values associated with the therapy parameter sets for comparison of the efficacies of the plurality of therapy parameter sets.

* * * * *

UNITED STATES PATENT AND TRADEMARK OFFICE
CERTIFICATE OF CORRECTION

PATENT NO. : 7,330,760 B2 Page 1 of 1
APPLICATION NO. : 10/826926
DATED : February 12, 2008
INVENTOR(S) : Kenneth T. Heruth It is certified that error appears in the above-identified patent and that said Letters Patent is hereby corrected as shown below:

Column 20
Line 2, "metric indicatin" should read -- metric indicating --.

Signed and Sealed this

Twenty-first Day of October, 2008

JON W. DUDAS
*Director of the United States Patent and Trademark Office*